United States Patent [19]
Farr

[11] 3,969,250
[45] July 13, 1976

[54] APPARATUS FOR PREPARING LIQUID SAMPLES FOR ANALYSIS IN AUTOMATIC ANALYZERS

[76] Inventor: Andrew F. Farr, 9321 Montemar Drive, Spring Valley, Calif. 92077

[22] Filed: Mar. 10, 1975

[21] Appl. No.: 556,784

[52] U.S. Cl. ............................. 210/359; 210/518; 210/DIG. 23
[51] Int. Cl.² ...................................... B01D 33/00
[58] Field of Search ............... 23/230 B, 258.5, 259; 128/2 F, 272, 218 M; 210/83, 84, 136, 359, 514–518, DIG. 23, DIG. 24

[56] References Cited
UNITED STATES PATENTS

| | | | |
|---|---|---|---|
| 3,512,940 | 5/1970 | Shapiro | 210/359 X |
| 3,661,265 | 5/1972 | Greenspan | 210/DIG. 23 |
| 3,701,434 | 10/1972 | Moore | 210/DIG. 24 |
| 3,832,141 | 8/1974 | Haldopoulos | 210/DIG. 23 |
| 3,846,077 | 11/1974 | Ohringer | 210/DIG. 23 |
| 3,865,731 | 2/1975 | Seitz | 210/359 |
| 3,894,951 | 7/1975 | Ayres | 210/136 |

Primary Examiner—Charles N. Hart
Assistant Examiner—Robert H. Spitzer
Attorney, Agent, or Firm—Miner L. Hartmann

[57] ABSTRACT

An improved device for filtering, isolating, containing, and storing fluid specimens which are to be analyzed with an automatic chemical analyzer. The device includes a filter means for removing particulates, a membrane valve for isolating the filtrate, a releasable piston ring which permits telescoping of the assembly, and a plunger tube which serves as a simple and/or storage vessel.

9 Claims, 7 Drawing Figures

U.S. Patent   July 13, 1976   3,969,250
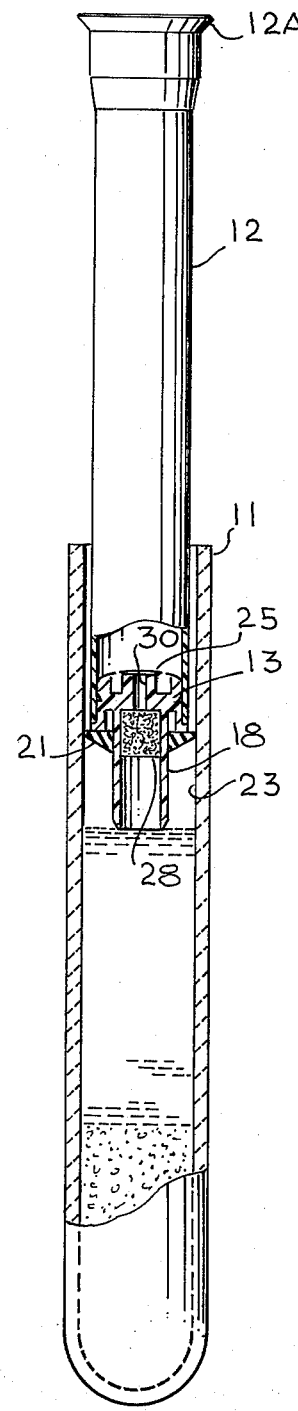
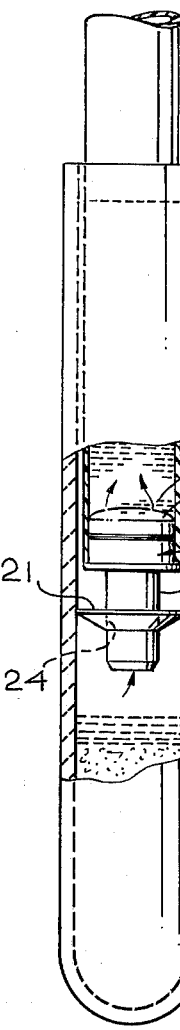
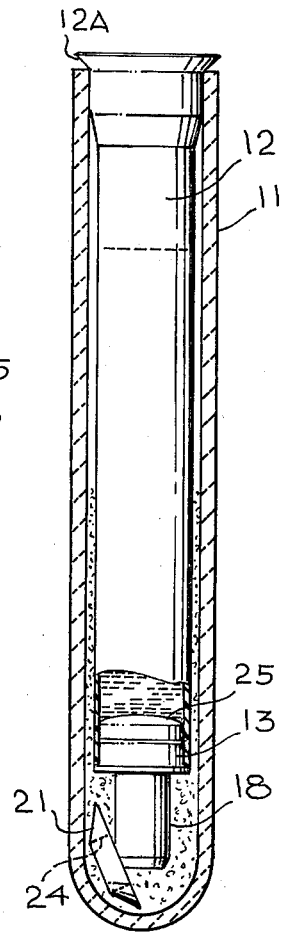
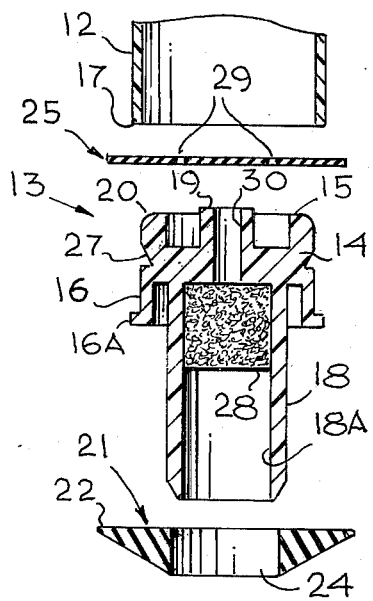
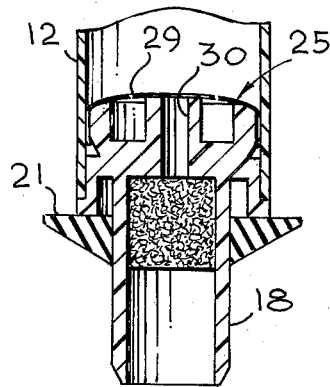
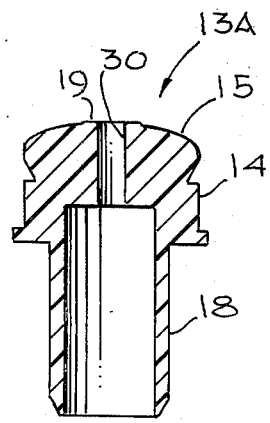
Fig. 1   Fig. 2   Fig. 3   Fig. 4   Fig. 5   Fig. 6   Fig. 7

APPARATUS FOR PREPARING LIQUID SAMPLES FOR ANALYSIS IN AUTOMATIC ANALYZERS

BACKGROUND OF THE INVENTION

This invention relates to a device which filters, isolates, and contains for sampling or storage, the supernatant fluid from a mixture of immiscible liquids or a slurry which has been stratified by centrifuging or standing. More specifically, it relates to a new and improved means for processing blood serum specimens which are to be used in automatic clinical chemistry analyzers.

In order to understand the conditions and problems inherent in clinical laboratory practice, the following discussions are pertinent.

1. Clinical laboratories employing automatic analyzers frequently process hundreds of blood specimens per day. Each individual specimen can require a wide variety of determinations. Often, more than one type of analyzer is needed to achieve the desired analyses. Obviously, maintaining the identity of large numbers of specimens and correlating multiple test results with the proper parent specimen is a problem of great complexity and importance. Errors in sample identification may conceivably contribute to the death of a patient.

2. The automatic sampling modules of existing clinical analyzers are limited in several ways by mechanical considerations. For instance, the vessels containing serum to be aspirated by the sampler must be of uniform dimensions, particularly height, so that the sample probe can enter them and function properly. This situation is normally met by transferring serum specimens for sampling to a series of uniform sample cups contained in a suitable rack. A problem arises, however, from such a transfer of serum to a sample cup in that the new cup requires labeling in some form, and this creates a potential source of identification errors.

3. Any volume of each serum specimen remaining after analysis is routinely stored in the clinical laboratory for several days so that check analyses can be made if necessary. Under most circumstances, such remaining serum volumes are decanted into special individual containers for refrigerated storage. The problem again arises that this additional transfer can require a further labeling operation and create another source of potential identification errors.

4. Still another problem arises in that each transfer of serum from one vessel to another creates a potential for chemical contamination of the specimen. Moreover, each transfer by decanting or pipetting creates a potential for contaminating the technical personnel with diseased serum.

5. Automated clinical chemistry analyzers themselves are often a problem because they are especially susceptible to clogging by small particles. Even serum which has been centrifuged still requires filtering.

6. It is well known that blood serum should be completely isolated from blood cells as soon as possible because ionic and osmotic exchanges take place, across cell walls, between serum and cells. Incomplete or delayed isolation of these blood components raise a potential problem of inaccurate analytical results.

SUMMARY

The present invention provides a device which filters, isolates, and serves as a subsequent sample container for the supernatant fluid from a mixture of immiscible liquids or a slurry which has been stratified. The device is particularly useful as a means for processing blood serum specimens which are to be used in automatic clinical chemistry analyzers. In general, it comprises an outer (parent) blood tube, an inner telescoping plunger tube, a piston head having a downwardly extending inlet tube upon which is mounted a slidingly removable piston seal, and a tension loaded diaphragm valve on the upper end of said depending inlet tube.

An important feature of my invention is that the plunger assembly can be telescoped down into the packed cell mass in the parent blood tube — after the serum has been isolated and filtered — without first removing said plunger tube or decanting the serum, a feature which has several important advantages:

a. Telescoping the plunger tube into the blood tube results in an assembly of uniform height where the top of the plunger tube is almost flush with the top of the parent blood tube. This minimal and uniform height of the assembly allows an automatic sampler to aspirate directly from the plunger tube positioned in its parent blood tube.

b. Decanting serum from the device is unnecessary, thus minimizing labor and possible contamination of the sample.

c. Sampling from the plunger tube disposed in its parent blood tube bearing the original identifying label avoids the labor of labeling an auxiliary vessel and minimizes identification errors.

d. Sampling from the plunger tube eliminates the cost of one or more auxiliary vessels.

e. Serum may be safely stored for reference in the telescoped assembly from which samples have been removed, thus avoiding the use of auxiliary sample vessels. This minimizes labor, possible contamination, and possible identification errors. It also eliminates the cost of auxiliary storage vessels.

f. Since decanting of serum or removal of the device from its parent tube is not required, possible contamination of personnel is minimized.

A second feature of the new device is that collected and filtered serum is isolated from packed blood cells by means of a mechanical barrier, thus preventing ionic or osmotic interchange even during long time storage.

A third feature of the new device is that, during use, the rubber piston ring is separated from the surface of the serum being collected by a column of trapped air. This feature precludes the wiping of cellular or other debris from the inner wall of the parent blood tube into the serum being collected. Contamination from this source could be of importance in certain analyses (e.g. enzymes).

A fourth feature of the device is that it may be used to advantage even in laboratories where analyses are performed manually.

This invention thus provides a means for processing blood serum for clinical chemistry analysis which: filters the serum; isolates serum from cells; provides an integral sample and storage vessel which is compatible with use in automatic sampling machines; minimizes potential sample contamination; minimizes sample identification errors; minimizes labor and equipment costs.

BRIEF DESCRIPTION OF THE DRAWINGS

FIG. 1 is a side-elevational view of an assembled tubular apparatus with parts broken away to show in section the interior arrangement of parts at the beginning of a filtration operation;

FIG. 2 is a similar view showing the parts after the separated serum has passed through the filter and valve into the plunger tube, and after the plunger tube has been retracted about one-fourth inch;

FIG. 3 is another view showing the relation of the parts after the filtration has been completed and the piston sealing ring has been displaced, and after the plunger tube has been telescoped completely down into the parent blood sample tube;

FIG. 4 is a disassembled view of the parts of the piston before assembly as a piston in the lower end of the plunger tube, shown in section;

FIG. 5 is an assembly of the piston parts in the lower end of the plunger tube, shown partly in section; and FIG. 6 is a fragmentary side elevation view of an optional enlargement of the upper end of the plunger tube; and FIG. 7 shows a side elevational view partly in section of an optional form of the rigid plastic piston body, whose upper surface is conical.

DESCRIPTION OF PREFERRED EMBODIMENTS

Referring to the drawings, the outer or blood tube 11 is a cylindrical tube of the kind in which blood samples are commonly delivered to the laboratory. An inner plastic plunger tube 12 is movably telescoped within the blood tube 11, its lower end being fitted with a piston head 13 which consists of a rigid plastic body 14 having an upwardly facing cup-shaped portion 15 with a depending skirt 16, whose outer surface closely fits inside the lower end of said plunger tube 12. The depending skirt 16 of the cylindrical body may also be provided with an out-turned rim 16A upon which the lower end 17 of the plunger tube 12 is positioned. The body 14 of the piston head has an integral depending tubular member 18 of smaller diameter than the cupped portion 15, the tubular member 18 communicating with the inside of the cup portion 15 through an apertured valve seat 19 which projects upwardly to, or slightly above, the height of the rim 20 of the upper portion 15. A flexible sealing ring 21 of rubber or other soft polymer, having a thinner outer portion 22 which makes sliding sealing contact with the inside wall 23 of the blood tube 11, and has a central opening 24 which makes sliding frictional contact on the outer surface of the depending tubular member 18.

An elastic membrane 25 is attached on or over the rim 20 of the upper portion 15 of the body 14, the membrane contacting at its center the upper surface of the valve seat 19. The membrane 25 is preferably a rubber dam of approximately 0.015 inches thickness, and is provided with one or more small openings 29 positioned away from the valve seat, for discharge of filtered serum into the upper part of the plunger tube 12.

The membrane is preferably attached over the upper portion 15 of the body 14 by stretching it during assembly between the lower end of the plunger tube 12 and the upper portion 15 of the body 14. The tension thus obtained is important in the valve function because it assures positive seating action of the membrane on the valve seat 19. The tension on the membrane can be varied in a predictable manner by altering certain design parameters of the rigid body 14. In this manner, it is possible to produce valves which will open only when pressure differentials exceeding pre-selected values are applied. A groove 27 may be provided in the outer cylindrical surface of the body 14 to receive the edge of the membrane 25.

The filter means 28 consists of fibrous or porous materials such as synthetic fibers, glass fibers, porous polymers, or the like, shaped into pads or plugs to frictionally fit in the tubular opening 18A. The filter material must not interfere with the chemistry of the serum passing through it. Fibrous cellulose acetate or sintered polyethylene are suitable if the effective pore size of the filter is in the range of 10 to 100 microns. The filter means 28 is frictionally fitted within the depending tubular member 18.

Optionally, the upwardly facing portion 15 of the body 14 is a conical surface except for the valve seat 19 with its orifice 30, as shown in FIG. 7.

The operation of the serum processing device will be understood by referring to FIGS. 1, 2 and 3. In FIG. 1, the plunger tube 12 is shown as just entering the blood sample tube 11 in which the blood cells have been settled out of the serum by the familar operation of centrifuging. The sealing ring 21, frictionally attached to the depending tubular member 18 of the piston head 13, makes sealing contact with the inside wall of the blood sample tube 11 above the level of the contained serum, and the lower end of the depending tube 18 makes contact with the surface of the serum. An air pocket is maintained between the sealing ring 21 and the top surface of the serum. Said air pocket prevents any intact blood cell, debris, or chemically active residue wiped from the inner wall of blood tube 11 by sealing ring 21, from contacting and contaminating the serum being filtered and collected as the piston is forced downwardly. The filtered serum passes through the opening 30 in valve seat 19, and exits through the small openings 29 in the membrane 25, into the plunger tube 12 above the piston head 13.

In use, as the lower end of the depending tubular member 18 reaches the mass of packed cells in the blood tube 11, the downward movement is halted. At this point in the operation, the user may follow either of two alternative procedures depending upon his need.

If the user intends to analyze the serum by manual methods, or if he chooses to decant aliquots of filtered serum for immediate use and store the remaining serum for future decanting, he would proceed as follows. The plunger tube 12 would be withdrawn one-eighth to one-fourth inches. Such upward motion would cause depending tubular member 18 to move slidingly upward in the central opening 24 of sealing ring 21. Said sealing ring would remain stationary because of friction on the walls of the blood tube and because of vacuum. This configuration of parts is shown in FIG. 2. It will be noted that both depending tubular member 18 and plunger tube 12, containing filtered serum, are completely isolated from the blood cells. It will be further noted that the air space above the cells remains sealed by sealing ring 21, and decanting of filtered serum may be accomplished without interference from cells. Storage of filtered serum in the parent blood tube carrying its original identification is convenient in this configuration.

Alternatively, should the user desire to process the filtered serum in an automatic analyzer, he would proceed as follows. Plunger tube 12 would be withdrawn three-eighths inch or more which would cause depending member 18 to slide completely out of central opening 24 of sealing ring 21. Sealing ring 21 would remain lodged in its horizontal position in blood tube 11. Now, the plunger tube 12 would again be moved downward into blood tube 11 and the depending member 18 would dislodge the sealing ring 21 and force it down into the blood cell mass. The plunger tube 12 would be further pushed down until its top enlargement is seated in the top portion of the blood tube 11. This configuration is shown in FIG. 3, the serum being isolated from cells by valve membrane 25. Tension placed upon membrane 25 during assembly of the device prevents upward flow of the cell-containing fluid even when the hydrostatic head of serum is reduced to zero.

Referring again to FIG. 3, it should be noted that the enlargement of the upper end, 12A, of plunger tube 12 serves several purposes. First, the enlargement forces positive alignment of the axis of plunger tube 12 and blood tube 11. Such alignment is necessary for the use of automatic sample probes. Second, the enlargement acts as a filler between the inner wall of blood tube 11 and the outer wall of plunger tube 12. Third, the enlargement serves to lock the plunger tube 12 to the blood tube 11 when these parts are fully telescoped. This feature minimizes the possibility of spilling red cells if the assembly is accidentally overturned during storage (plunger tube 11 would normally be stoppered for storage).

The configuration shown in FIG. 3 permits a suitable automatic sampling machine such as those used with clinical chemistry analyzers, to withdraw aliquots from a rack of tubes having uniform and minimal heights.

The advantages of my invention will be clear from the above description of the parts and their functioning in use.

I claim:

1. An apparatus for separating a clear blood serum free from fibrin strands and other suspended solids comprising:
    a. an outer tubular member, closed at the lower end;
    b. a plunger tube longitudinally movable within said outer member;
    c. a piston head attached to the lower end of said plunger tube, said piston head comprising a body having a cup-shaped upper portion with a depending skirt whose outer surface fits inside the lower end of said plunger tube, said body also having a depending tubular member communicating with said cup-shaped upper portion of the body through an apertured valve seat projecting upwardly to at least the height of the rim of said upper portion;
    d. a flexible sealing ring whose outer periphery makes sliding sealing contact with the inside wall of said outer tubular member, said ring being frictionally attached to and movable axially on the outer surface of the said depending tubular member of said body;
    e. an elastic membrane extending across said cupped upper portion of the body so that said membrane covers the opening of said valve seat, said membrane having at least one opening therethrough positioned away from the valve seat; and
    f. a filter means frictionally fitted into said depending tubular member of said body.

2. The apparatus defined in claim 1, in which said body is rigid.

3. The apparatus defined in claim 2, in which said depending skirt of said body has an out-turned rim for positioning the lower end of said plunger tube.

4. The apparatus defined in claim 2 in which the elastic membrane is stretched over the rim of said cupped portion of said body, the outer margin of said membrane being held between the outer wall of said cupped upper portion and the inside wall of said plunger tube.

5. The apparatus defined in claim 2 in which said sealing ring is slidably removable from the free end of said depending tubular member of said body.

6. The apparatus defined in claim 2, in which said plunger tube at its upper end is enlarged to slidingly fit within the upper end of the outer tubular member.

7. An apparatus for separating a clear blood serum from fibrin strands and other suspended solids comprising
    a. an outer tubular member, closed at the lower end;
    b. a plunger tube longitudinally movable within said outer member;
    c. a piston head attached to the inner end of said plunger tube, said piston head comprising a cylindrical body whose outer surface fits inside the lower end of said plunger tube, said body also having a depending tubular member communicating with the upper surface of the cylindrical body through an apertured valve seat projecting upwardly to at least the height of the rim of said cylindrical body;
    d. a flexible sealing ring whose outer periphery makes sliding sealing contact with the inside wall of said outer tubular member, said ring being frictionally attached to and movable axially on the outer surface of the said depending tubular member of said body;
    e. an elastic membrane extending across the top of said cylindrical body so that said membrane covers the opening of said valve seat, said membrane having at least one opening therethrough positioned away from the valve seat; and
    f. a filter means frictionally fitted into said depending tubular member of said body.

8. The apparatus defined in claim 7 in which the upper surface of said cylindrical body is a flat cone sloping away from said valve seat.

9. The apparatus defined in claim 7, in which the elastic membrane is pre-tensioned.

* * * * *